(12) United States Patent
Strassl et al.

(10) Patent No.: US 7,780,655 B2
(45) Date of Patent: Aug. 24, 2010

(54) MEDICAL OR COSMETIC HAND-HELD LASER DEVICE

(75) Inventors: Martin Strassl, Salzburg (AU); Thomas Irran, Salzburg (AU)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 102 days.

(21) Appl. No.: 11/807,970

(22) Filed: May 30, 2007

(65) Prior Publication Data

US 2007/0282315 A1 Dec. 6, 2007

(30) Foreign Application Priority Data

Jun. 6, 2006 (EP) .................................. 06011590

(51) Int. Cl.
*A61B 18/18* (2006.01)
(52) U.S. Cl. .............................. 606/18; 606/13; 607/88
(58) Field of Classification Search ............. 433/29–31, 433/43
See application file for complete search history.

(56) References Cited

U.S. PATENT DOCUMENTS

| | | | | |
|---|---|---|---|---|
| 3,090,931 A | * | 5/1963 | Marcatili | 333/249 |
| 4,094,578 A | * | 6/1978 | DiVita et al. | 385/51 |
| 4,274,705 A | * | 6/1981 | Miller | 385/12 |
| 5,088,924 A | * | 2/1992 | Woodward | 433/126 |
| 5,741,244 A | * | 4/1998 | Klaas | 606/4 |
| 6,325,794 B1 | | 12/2001 | Yoon et al. | |
| 6,594,539 B1 | | 7/2003 | Geng | |
| 6,636,759 B2 | | 10/2003 | Robinson | |
| 2002/0138073 A1 | * | 9/2002 | Intintoli et al. | 606/15 |
| 2003/0228094 A1 | | 12/2003 | Rizoiu et al. | |
| 2004/0214132 A1 | * | 10/2004 | Altshuler | 433/29 |
| 2005/0215987 A1 | * | 9/2005 | Slatkine | 606/9 |
| 2005/0256516 A1 | | 11/2005 | Boutoussov | |

FOREIGN PATENT DOCUMENTS

DE 37 135 12 10/1987

OTHER PUBLICATIONS

European Search Report for European Patent Application No. EP 06 01 1590.

* cited by examiner

*Primary Examiner*—Henry M Johnson, III
*Assistant Examiner*—Lynsey Crandall
(74) *Attorney, Agent, or Firm*—Klarquist Sparkman, LLP

(57) ABSTRACT

A medical or cosmetic hand-held laser device with an optical waveguide device is subdivided into a first section and a second section arranged at an angle thereto for emitting laser radiation onto a treatment area. To deflect the laser beam from the first section into the second section as effectively as possible and in particular to launch the laser beam with the lowest possible loss into a waveguide that conducts the laser beam further, the hand-held device is provided with a reflector that is arranged between the two sections and has an essentially elliptical reflective surface.

12 Claims, 1 Drawing Sheet

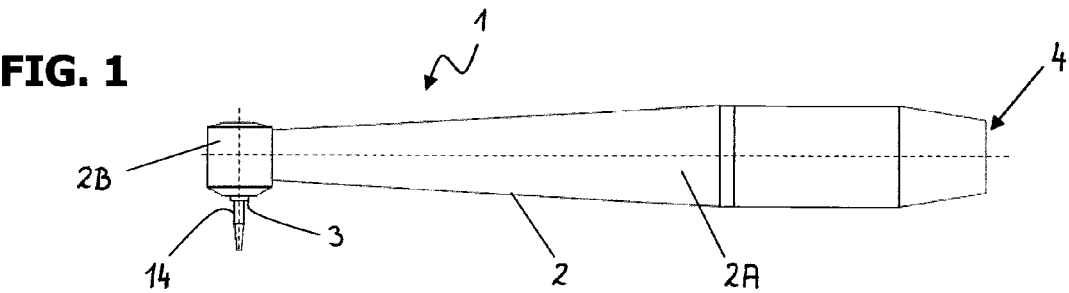
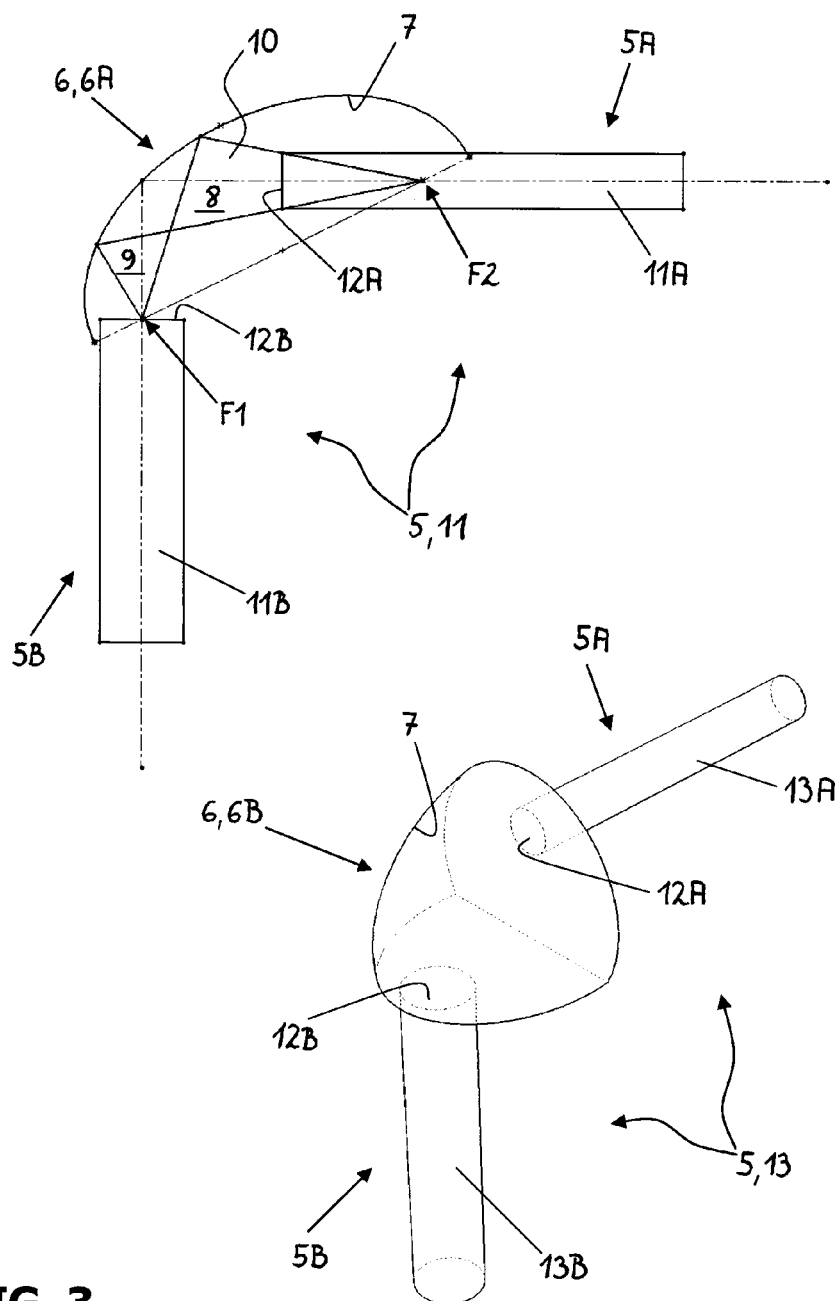

MEDICAL OR COSMETIC HAND-HELD LASER DEVICE

CROSS REFERENCE TO RELATED APPLICATION

The present application claims priority from pending European Patent Application No. 06011590.4, filed Jun. 6, 2006, which is incorporated herein by reference.

BACKGROUND

1. Field

The present application relates to a medical or cosmetic hand-held device for emitting laser radiation to a treatment location.

2. Description of Prior Art

Such a hand-held laser device is known from the German patent application DE 37 135 12 A1, for example. It comprises a handle part and a head part arranged at an angle thereto with the beam exit opening. A reflector designed as a concave mirror is provided to deflect the laser beam from the handle part into the head part and into the light exit opening. As an alternative, other optical elements such as lenses, flat mirrors or prisms are also known for deflecting the laser beam.

All known optical deflection elements have various disadvantages, e.g., inaccurate focusing or none at all and the associated power loss, complexity of installation in the hand-held device or cost-intensive production.

One goal is therefore to create a hand-held device having an improved optical element for deflection of the laser beam. The optical element should deflect the laser beam as effectively as possible and in particular should launch the largest possible portion of the laser beam into an optical waveguide device that routes the laser beam. The improved optical element should thus make the entire deflection operation as low-loss as possible.

SUMMARY

Described below are embodiments of a hand-held laser device that addresses some of the shortcomings of the prior art.

The hand-held laser device has a reflector with a reflective surface designed to be essentially elliptical for deflecting the laser beam from the first section of the optical waveguide device into the second section arranged at an angle thereto. The elliptical reflective surface in particular has the advantage that focusing of the laser beam is definitely improved in comparison with all known optical elements used in medical or cosmetic hand-held laser devices. The beam, which is guided essentially through the first focal point of the elliptical reflective surface, is deflected to the second focal point of the elliptical reflective surface regardless of its angle of emergence, so that the deflection is accomplished with significantly lower losses than is the case with the known optical element. This effect is especially important with the manually guided medical or cosmetic hand-held laser devices, because the hand-held devices are often connected to the laser light source via rotating joints or couplings, which permit the user free rotatability and therefore simplified handling, and the laser beam is supplied to the hand-held device over an optical waveguide. Since the hand-held device is guided by hand and has a rotating joint, the fiber optic guide often has a slight play in movement with respect to the reflector, so the angle of emergence of the beam varies in the direction of the reflector. A reflector having an elliptical reflective surface is able to compensate for such variations better than the known optical deflection elements in medical or cosmetic hand-held devices.

However, the reflector with the essentially elliptical reflective surface has other advantages: it causes simultaneous deflection and focusing so that only one optical element is needed for both tasks. The spherical aberration with respect to other known optical deflection elements which are used in medical or cosmetic hand-held laser devices is also reduced, which is important for medical or cosmetic treatments in particular because in this case the radiation should strike only the treatment area, which is often very small, and the tissue surrounding the treatment area should remain as free of radiation as possible. Finally, an elliptical reflector permits a considerable freedom in design (for example, with respect to the dimensions of the two axes and/or the ratio of the axial lengths to one another, the distance between the two focal points, the radius of curvature, etc.), so the elliptical reflector can be adapted to the spatial conditions prevailing in the hand-held device without losing the aforementioned advantages, in particular the improved focusing.

In a first exemplary embodiment, the reflector with the elliptical reflective surface may be designed as a concave mirror. This has the advantage that the entire reflector has a low weight, which plays an important role, especially in medical or cosmetic hand-held laser devices which are held in the hand by the user for a long period of time. In a second exemplary embodiment, the reflector is designed as a solid body, i.e., as an optical waveguide in the form of a body that has an elliptical reflective surface and is transparent for the laser beam. The advantage of the solid body lies in the better reflection properties (total reflection) in comparison with the concave mirror and the simpler production because the elliptical reflective surface is designed as a concave exterior surface.

In a second exemplary embodiment, the end of at least one section of the optical waveguide device facing the reflector is arranged substantially at one of the focal points of the elliptical reflective surface. In a preferred exemplary embodiment, the end of at least one section of the optical waveguide device facing the reflector, in particular the end of a glass rod or a glass fiber rod, is arranged between one of the focal points and the reflective surface. That is, the reflector is arranged with respect to the optical waveguide device, so that at least one focal point of the elliptical reflective surface is shifted to a section of the optical waveguide device, essentially to the areas of the optical waveguide device where the tip of the output cone and/or the tip of the acceptance cone of the laser beam is/are formed. This advantageously yields a further increase in luminous efficiency because a greater portion of the laser beam passing through the optical waveguide device is deflected by the reflector and strikes the second section of the optical waveguide device.

In another preferred exemplary embodiment, the geometry of the essentially elliptical reflective surface corresponds to a partial area of the surface of an ellipsoid, i.e., it corresponds to a section of the surface of an ellipse rotating about its axes, in particular its main axis. Due to this geometric design, the main intensity of the deflected laser beam is imaged on the second section of the optical waveguide device in a concentrated entrance pupil that is approximately circular or point-shaped, whereby the area of the entrance pupil is preferably smaller than the entrance area of the second section of the optical waveguide device, thus launching the laser beam with the lowest possible loss.

The optical waveguide device and/or each of the two sections of the optical waveguide device consists of a bore running through the hand-held device, designed either as a beam path for conducting a free beam or as a receptacle for a glass rod or an optical fiber, in particular a glass fiber rod. The glass rod or the optical fiber may be fixedly attached to the hand-held device and may thus be part of the hand-held device or may be detachably accommodatable in the hand-held device. The greatest effect with respect to optimal focusing with the lowest possible loss is achieved when a glass rod or an optical fiber is used for conducting the laser beam. The angle between the sections of the optical waveguide device may vary in a wide range between 5° and 90°. In some implementations, the range varies from 5° to 40°, preferably 15° to 20°. In a first embodiment, the range varies from 45° to 88°, preferably 55° to 65°. The range varies from 70° to 75° in another embodiment.

The reflector with the elliptical reflective surface may comprise a metallic base body, e.g., made of copper, steel or nonferrous metals, or a dielectric base body, e.g., made of optical glass, in particular quartz glass, zinc selenide glass or calcium fluoride glass, ceramics or plastics. The reflector may also have a metallic coating, e.g., made of copper, steel or nonferrous metals, or a dielectric coating, preferably produced by vapor deposition. To protect against corrosion, the reflective surface may additionally comprise an oxide layer, e.g., a silver oxide layer or a copper oxide layer. Multilayer systems consisting of multiple layers of coatings applied to the base body may also be preferred, resulting in dichroic coatings or so-called chirped coatings, e.g., coatings that correct for deviating transit times of radiation comprising multiple wavelengths. Finally, the reflector may also have three-dimensional structures, e.g., grooves or shallow recesses on its reflective surface, to impose especially advantageous shapes and intensity distributions on the reflected beam via additional reflective effects, refractive effects or diffraction effects.

The characteristic values of an elliptical reflector installed in one embodiment of a medical or cosmetic hand-held laser device may be approximately as follows:
  axial ratio of the main axis to the secondary axis: 1.25-6, preferably 1.3-4, especially preferably 1.45.
  focal distance: 1.5-5.9 mm, preferably 1.6-4 mm, especially preferably 1.98 mm.
  numerical eccentricity: 0.5-0.9, preferably 0.6-0.8, especially preferably 0.725.

Implementations of the device are explained in greater detail below on the basis of preferred exemplary embodiments and with reference to the accompanying drawings.

BRIEF DESCRIPTION OF THE DRAWINGS

FIG. 1 shows an exemplary embodiment of a medical or cosmetic hand-held laser device.

FIG. 2 shows a schematic diagram of a reflector contained in a hand-held laser device having an elliptical reflective surface in the form of a concave mirror.

FIG. 3 shows a schematic diagram of a reflector having an elliptical reflective surface in the form of a solid body contained in a hand-held laser device.

DETAILED DESCRIPTION

The medical or cosmetic hand-held laser device 1 illustrated in FIG. 1 can be used in particular for dental treatments. It comprises an elongated cylindrical outer sleeve 2 that is hollow on the inside and is subdivided into a handle part 2A and a head part 2B. The handle part 2A and head part 2B are arranged at an angle to one another, with the angle being approximately 90°. Handle part 2A and head part 2B may be manufactured in two parts and joined together or they may be manufactured from one workpiece. On the end of the handle part 2A opposite the head part 2B, there is a connecting device 4 for connecting the hand-held laser device 1 to a source of laser beam (not shown). Since the connecting device and/or the various types of connecting devices that can be used with such a hand-held device 1 are known, details are not given here. A rotating joint that allows the user free rotatability and thus good handling of the hand-held device 1 is preferably provided as the connecting device 4. The rotating joint and the hand-held device 1 are especially preferably designed so that they can be connected to a supply tubing with an optical fiber protruding beyond the supply tubing. The optical fiber is inserted into the hand-held device 1 only while the hand-held device 1 is coupled to the supply tubing, in which case it extends preferably to the vicinity of the head part 2B or into the head part 2B.

At the distal end of the outer sleeve 2, especially in the head part 2B, a light exit opening 3 is provided at the side so that laser beam 10 (FIG. 2) can be emitted onto a treatment location. Preferably an optical fiber 14, e.g., a so-called sapphire tip, is or may be inserted into the head part 2B, conducting the laser beam 10 through the light exit opening 3 to the treatment location. The distal end of the optical fiber 14 may preferably be designed so that the optical fiber 14 can also be placed directly on the treatment location, so that targeted application of the laser beam and support of the hand-held device 1 are possible.

An optical waveguide device 5 which is subdivided into a first section 5A and a second section 5B arranged at an angle to the former, extends through the hand-held device 1 from the connecting device 4 to the light exit opening 3. The optical waveguide device 5 comprises a first bore and a second bore corresponding to the sections 5A, 5B and optical waveguides that can be accommodated therein, e.g., in the form of an optical glass fiber rod 11, an optical crystal, in particular a sapphire crystals or a glass rod 13, which also have a first section 11A, 13A and a second section 11B, 13B arranged at an angle thereto (see FIGS. 2 and 3). The sections 5A, 11A, 13A of the optical waveguide device 5 are arranged in the handle part 2A, and sections 5B, 11B, 13B are arranged in the head part 2B of the hand-held device 1. Section 11A is preferably the end piece of the waveguide accommodated in the supply line, by means of which the hand-held device 1 can be connected to the laser light source. The end piece protrudes beyond the coupling section of the supply line so that, when the hand-held device 1 is connected to the supply line, this end piece can be inserted into the bore of the handle part 2A and protrudes up to or into the head part 2B of the hand-held device 1. Section 11B of the optical waveguide device 5 may preferably be designed as part of the optical fiber 14.

FIG. 2 shows in a schematic diagram how the laser beam 10 is transmitted from the first section 5A into the second section 5B, which is arranged at an angle to the former, of the optical waveguide device 5. A reflector 6 whose reflective surface 7 is designed to be essentially elliptical, preferably as a partial face of an ellipsoid, is arranged between the two sections 5A and 5B. The glass fiber rod 11 A as part of the first section 5A conducts the laser beam 10 in the direction of the reflector 6 and emits it at its end 12A that faces the reflector 6. The laser beam 10 emitted strikes the reflector 6, designed as a concave mirror 6A, and is deflected by it into the second section 5B of the optical waveguide device 5 with the fiberglass rod 11B and conducted further in the direction of the treatment location. The elliptical reflective surface 7 has two focal points F1, F2, whereby each beam of the laser beam 10 emitted is reflected from one focal point F1 into the second focal point F2.

FIG. 2 also shows that the sections 5A, 11A and/or 5B, 11B of the optical waveguide device 5 may be arranged differently with respect to the reflector 6. The end 12A of the fiberglass section 11A and of section 5A facing the reflector 6 is arranged between the focal point F2 and the reflective surface 7. Section 5A thus penetrates into the cavity of the concave mirror 6A. Therefore focal point F2 is shifted into the sections 5A, 11A of the optical waveguide device 5, essentially into the areas of the sections 5A, 11A where the tip of the output cone 8 of the laser beam 10 is formed. In contrast with that, the end 12B of the section 5B of the optical waveguide device 5 facing the reflector 6 is essentially in the focal point F1 of the elliptical reflective surface 7. The acceptance cone 9 of the laser beam 10 here is outside of sections 5B, 11B, accordingly.

The embodiment illustrated in FIG. 2 represents the most effective arrangement of the sections 5A, 5B, 11A, 11B because due to the displacement of the sections 5A, 11A into the concave mirror 6A and due to the positioning of the sections 5B, 11B essentially in the focal point F1, an especially effective deflection is achieved, i.e., an especially great amount of laser beam 10 is launched into the sections 5B, 11B so that it can also be routed further. Nevertheless, the embodiment shown here is only exemplary, and, if technically necessary or expedient, the sections 5B, 11 B may also be inserted into the concave mirror 6A, e.g., if space conditions are tight, and/or the end 12A of the sections 5A, 11A may be situated essentially in the focal point F2.

The exemplary embodiment shown in FIG. 3 corresponds in function and essential design to that from FIG. 2, so that the same components are provided with the same reference numerals. In contrast with FIG. 2, the reflector 6 is designed as a solid body 6B with a base body comprising optical glass such as quartz glass, for example, whereby a side wall of this base body is shaped as an essentially elliptical reflective surface 7, preferably as a partial area of the surface of an ellipsoid. The reflector 6 is thus itself an optical waveguide, whereby the laser beam is guided through the section 5A comprising the glass rod 13A to the solid body 6B and through the latter to the reflective surface 7. After being deflected on the reflective surface 7, the laser beam enters the glass rod 13B of section 5B and is routed further in the direction of the treatment area. As described with respect to FIG. 2, one or both ends 12 of the glass rods 13A, 13B may in turn be arranged essentially at the focal point F1, F2 of the reflective surface 7 or between the focal point F1, F2 and the reflective surface 7. In addition there is the possibility of accommodating at least one of the ends 12 in a blind hole in the solid body 6B, so that assembly of the optical waveguide device 5 with the reflector 6 is simplified and the positioning of the optical waveguide device 5 in relation to the reflective surface 7 is stabilized.

The dimensions of the reflectors 6 shown in FIGS. 2 and 3 amount to approximately 3.0 mm×7.0 mm×3.5 mm (length× width×height).

The invention is not limited to the exemplary embodiments described here, but instead includes all possible embodiments that do not alter the basic function principle of the invention accordingly. In particular such hand-held devices may be used not only for dental treatments but also for many other cosmetic or medical treatments such as ophthalmic procedures, for removing hair or moles, in vascular medicine or for diagnostic applications.

What is claimed is:

1. A medical or cosmetic hand-held laser device, comprising:
   a light exit opening for emitting laser radiation onto a treatment area;
   a connecting device for connecting the hand-held laser device to a source for laser radiation;
   an optical waveguide device extending from the connecting device to the light exit opening, the optical waveguide device has a first section, a second section arranged at an angle to the first section, and a reflector arranged between the first and second sections with a substantially elliptical reflective surface for deflecting the laser radiation from the first section into the second section of the optical waveguide device and for creating an output cone of laser radiation emitted from the first section and a converging beam of laser radiation for receipt by the second section;
   the first section having a first end, opposite an end for receiving the laser radiation in the first section generated by the source, that penetrates a cavity of the reflector so that a first focal point of the reflector is within the first section and spaced apart from the first end, the first focal point being a tip from which the output cone of laser radiation is to be formed;
   the second section having a second end, opposite an end of the second section for emitting the laser radiation towards the treatment area, that is positioned with respect to the reflector surface so that a second focal point of the reflector is substantially coincident with the second end, so that the first and second sections are arranged differently with respect to their associated first and second focal points.

2. The hand-held laser device according to claim 1, wherein the first section is cylindrical and is removably coupled to the hand-held laser device.

3. The hand-held laser device according to claim 1, wherein the second focal point is positioned so that the converging beam of laser radiation is outside of the second section and converges at the second focal point.

4. The hand-held laser device according to claim 1, wherein the substantially elliptical reflective surface is designed as a section of the surface of an ellipsoid.

5. The hand-held laser device according to claim 1, wherein the reflector is designed as a concave mirror or as a solid body.

6. The hand-held laser device according to claim 1, wherein a rotating joint is provided as the connecting device.

7. The hand-held laser device according to claim 1, wherein the reflector comprises a metallic or dielectric base body.

8. The hand-held laser device according to claim 1, wherein the substantially elliptical reflective surface comprises a metallic or dielectric coating and/or an oxide layer.

9. The hand-held laser device according to claim 1, wherein the optical waveguide device comprises at least one of a bore, at least one glass rod, an optical crystal and an optical fiber.

10. The hand-held laser device according to claim 1, wherein at least one of the first and second sections comprises a glass fiber rod.

11. The hand-held laser device according to claim 1, wherein the reflector is designed as a solid body.

12. The hand-held laser device according to claim 1, wherein the laser radiation is guided through the first focal point of the substantially elliptical reflective surface and is deflected to the second focal point of the substantially elliptical reflective surface regardless of its angle of emergence from the optical waveguide device.

* * * * *